United States Patent [19]

DeYoung

[11] Patent Number: 4,605,671

[45] Date of Patent: Aug. 12, 1986

[54] PARENTERAL FORMULATION

[75] Inventor: Joyce L. DeYoung, Wayne, Pa.

[73] Assignee: American Home Products Corporation, New York, N.Y.

[21] Appl. No.: 757,992

[22] Filed: Jul. 23, 1985

Related U.S. Application Data

[63] Continuation-in-part of Ser. No. 655,976, Sep. 28, 1984, abandoned.

[51] Int. Cl.$^4$ ............................................. A61U 31/135
[52] U.S. Cl. ...................................................... 514/647
[58] Field of Search ........................................... 514/647

[56] References Cited

PUBLICATIONS

Merck Index, 9th Ed (1976) 1017.
Remington's Pharmaceutical Science 16th ed (1980), pp. 1225–1227, 700–701.
Oosterlinck et al., Curr. Med. Res. Opin. 6 472–474, (1980).
Staquet, Curr. Med. Res-Opin. 6 634–637, (1980).
Molis et al., J. Pharmacol Exp. Ther. 194, 488–498, ©1975.

*Primary Examiner*—Stanley J. Friedman
*Attorney, Agent, or Firm*—Richard K. Jackson

[57] ABSTRACT

Ready-to-use parenteral formulations of Dezocine containing from about 0.2 to about 2.0 percent wt/vol. Dezocine; about 30 to about 45 percent wt/vol. propylene glycol; about 0.5 to about 2.0 percent wt/vol. lactic acid buffered with a pharmaceutically acceptable base to a pH of from about 3.5 to about 5.0 and 0 to 0.02 percent wt/vol. sodium metabisulfite, in water for injection.

6 Claims, No Drawings

PARENTERAL FORMULATION

RELATED APPLICATION

This application is a continuation-in-part of U.S. Ser. No. 655,976, filed Sept. 28, 1984, now abandoned.

BACKGROUND OF THE INVENTION

Dezocine[(−)-13β-amino-5,6,7,8,9,10,11,12-octahydro-5α-methyl-5,11-methanobenzocyclodecen-3-ol] is an orally and parenterally active analgesic agent possessing a narcotic antagonist activity. As the hydrobromide salt, Dezocine is a pale, cream-colored odorless crystalline powder which is soluble in water at a concentration greater than 20 mg/ml. Initial clinical studies employing this drug at concentrations of 1, 2, 3, 4, and 5 mg/ml. in saline were conducted with lyophilized product reconstituted at the time of administration.

DESCRIPTION OF THE INVENTION

It has now been discovered that ready-made injectable solutions of Dezocine hydrobromide discolor and/or form insoluble material in less than one year when stored at room temperature and at 35° C. In addition, many of the solutions prepared using the base form of Dezocine also form insoluble material. The insoluble material formed is generally a fine, light-colored and amorphous solid. However, in one instance (Formulation A, infra) insoluble crystals were produced in sufficient quantity to permit identification as dezocine sulfate, a product of oxidation of the metabisulfite to sulfate. The other insoluble materials are of unknown constitution. In the presence of monothioglycerol employed as an antioxidant, up to about a 10 percent potency loss in six months at room temperature storage has been observed.

Because it is most desirable to provide ready-made injectables with a room temperature shelf life of approximately two years, an improved injectable formulation for parenteral administration is needed.

Thus, in accordance with this invention there is provided a stable, parenteral, aqueous solution of a therapeutically effective amount of Dezocine[(−)-13β-amino-5,6,7,8,9,10,11,12-octahydro-5α-methyl-5,11-methanobenzocyclodecen-3-ol] consisting essentially of from 0.2 to about 2.0 percent weight/volume of [(−)-13β-amino-5,6,7,8,9,10,11,12-octahydro-5α-methyl-5,11-methanobenzocyclodecen-3-ol]; from about 30 to about 45 percent weight/volume of propylene glycol; from about 0.5 to about 2.0 percent weight/volume of lactic acid; buffered with a pharmaceutically acceptable base to afford a pH of from about 3.5 to about 5.0; and from 0 to 0.02 percent weight/volume of sodium or potassium metabisulfite, in water for injection.

Preferred formulations for parenteral administration contain, in water for injection, from about 0.5 to about 1.5 percent weight per volume dezocine; about 0.0075 to about 0.015 percent weight per volume sodium metabisulfite; about 0.6 to about 1.0 percent weight per volume lactic acid; about 30 to about 42.5 percent weight per volume propylene glycol; and enough sodium hydroxide to produce a pH of 3.5 to 5.0. Because the formation of dezocine sulfate can occur, as noted supra, the amount of sodium metabisulfite present is decreased with increased quantities of drug to insure the theoretical maximum dezocine sulfate formation is solubilized. Thus, it is preferred to limit the metabisulfite to a maximum of 0.025 percent for 0.5 percent dezocine; 0.015 percent for 1.0 percent dezocine; and 0.005 percent for 2.0 percent dezocine.

The formulations of this invention are self-preserving [as established by the technique published in U.S. Pharmacopeia XX, pp. 873–874(1980)] and need no additive preservative ingredient. The formulations of the invention all demonstrate acceptable storage stability throughout the drug concentration for at least twenty-four months at room temperature when made-up in ampuls, Tubex ® cartridges, and vials, employing several different elastomers in the vial and Tubex ® closures. At elevated temperatures under accelerated storage test conditions (6 months at 45° C. or 18 months at 35° C.), some insoluble formation occurred in a few cases in the absence of an antioxidant. Therefore, the formulations containing an antioxidant are preferred. The main difference between the formulations containing an antioxidant and those with no antioxidant is that the latter darken more, although they remain acceptable for at least 24 months stored at room temperature.

Thus, the formulations of this invention provide solutions of Dezocine suitable for parenteral injection. These new formulations are stable in storage for at least two years and provide a dosage form which may be maintained in ready-to-use form thereby avoiding separate packaging of diluent and drug and the necessity for reconstitution at the time of administration.

Although propylene glycol has been used heretofore as a non-aqueous solvent for the purpose of improving aqueous solubility of active drug substances and is classified as a non-aqueous solvent, it is not employed for that purpose in the formulation of this invention. Dezocine, in the form of its acid addition salts, is very soluble in water (greater than 100 mg/mL $H_2O$ in lactic acid buffer at pH 4 to 5) and needs no additional solvent. For purposes of this invention, propylene glycol has been found to prevent the formation of unknown trace insolubles which develop in completely aqueous formulations containing Dezocine.

Specifically preferred formulations of this invention contain 0.5, 1.0, 1.5 and 2.0 percent weight per volume of Dezocine and are constituted as follows:

|  | Percent (wt/vol) | | | |
| --- | --- | --- | --- | --- |
| Dezocine | 0.5 | 1.0 | 1.5 | 2.0 |
| Sodium Metabisulfate | 0.015 | 0.015 | 0.0075 | 0.005 |
| Propylene Glycol | 31 | 31 | 31 | 31 |
| Lactic Acid | 0.6 | 0.8 | 1.0 | 1.3 |
| NaOH | qs pH 4.0 | qs pH 4.0 | qs pH 4.0 | qs pH 4.0 |
| $H_2O$ | qs 1 mL | qs 1 mL | qs 1 mL | qs 1 mL |

Although other orders of mixing are possible, the formulations of this invention are most readily prepared by dissolving the lactic acid and sodium or potassium metabisulfite in a portion of the water for injection, dissolving the Dezocine in this solution, adjusting the pH, adding the propylene glycol and mixing thoroughly before making the final volume adjustment.

The following formulations for parenteral administration of Dezocine illustrate additional unsuccessful attempts to prevent the formation of insoluble material in ready-made unit dosage forms, as well as stable formulations of this invention. Table I presents formulations in addition to the simple saline solutions and aqueous solutions referred to supra, which do not avoid the problem of insolubles formation and Table II presents formulations which do avoid the problem. The acceptability or unacceptability of a given formulation was determined by filling the experimental formulations into packages (ampules, vials, Tubex ® cartridges, etc.) of the type and sizes conventionally used with parenteral drugs. These packages were stored at temperatures from 5° C. to 60° C. At various times, samples were examined for color change and development of insoluble material. The pH was measured and chemical assays performed to ascertain whether significant chemical loss had occurred and to assure maintenance of potency. If a sample developed insolubles at any time during its projected shelf-life (two years at room temperature) it was considered unsuitable. Although formulations N and O did not produce insolubles in stability studies in ampules, vials, or Tubex ® cartridges, they are considered unacceptable because from calculations based upon equilibrium solubility measurements there is sufficient sodium metabisulfite present that, were it to all be oxidized to sulfate, the dezocine sulfate could exceed saturation and precipitate at room temperature. Otherwise, all of the formulations in Table I developed insoluble material at one or more time-temperature points. In addition, many of them discolored markedly. These problems did not occur with samples stored at room temperature with formulation taken from Table II.

TABLE I

| Active Ingredient | Unacceptable Formulations - % (wt/vol) | | | | | | | |
|---|---|---|---|---|---|---|---|---|
| | A | B | C | D | E | F | G | H |
| Dezocine | 1.5 | 10.3 | 10.3 | 2.0 | 2.0 | 2.0 | 1.5 | 2.0 |
| Antioxidants | | | | | | | | |
| Sodium Metabisulfite | 0.025 | — | — | — | — | — | — | — |
| Ascorbic Acid | — | — | — | — | — | 0.50 | — | — |
| Monothioglycerol | — | — | — | — | — | — | — | 0.5 |
| Cysteine.HCl | — | — | — | 0.20 | — | — | — | 0.2 |
| Propyl Gallate | — | — | — | — | — | — | 0.02 or 0.10 | — |
| Solubilizing Agents | | | | | | | | |
| Benzethonium chloride | — | — | — | — | — | — | — | — |
| Propylene Glycol | — | — | — | — | 21 | 21 | 31 | 42 |
| Buffer | | | | | | | | |
| Lactic Acid | 1.3 | 8.4 | 8.4 | 1.7 | 1.7 | 1.7 | 1.0 | 1.7 |
| Sodium Hydroxide | q.s. pH 4.5 | q.s. pH 4.5 | q.s. pH 4.5 | q.s. pH 4.0 or pH 4.5 | q.s. pH 4.0 | q.s. pH 4.0 | q.s. pH 4.0 | q.s. pH 4.0 |
| Preservative | | | | | | | | |
| Methyl Paraben | 0.10 | 0.10 | — | — | — | — | — | — |
| Diluent | | | | | | | | |
| $H_2O$ | qs | qs | qs | qs | qs | qs | qs | qs |

| Active Ingredient | I | J | K | L | M | N | O |
|---|---|---|---|---|---|---|---|
| Dezocine | 2.0 | 2.0 | 2.0 | 2.0 | 2.0 | 1.5 | 1.0 |
| Antioxidants | | | | | | | |
| Sodium Metabisulfite | — | — | — | — | — | 0.025 | 0.025 |
| Ascorbic Acid | — | — | — | — | — | — | — |
| Monothioglycerol | 0.5 | — | 0.5 | 0.5 | 0.5 | — | — |
| Cystein.HCl | — | 0.2 | 0.2 | — | — | — | — |
| Propyl Gallate | — | — | — | — | — | — | — |
| Solubilizing Agents | | | | | | | |
| Benzethonium chloride | — | — | — | — | 0.01 | — | — |
| Propylene Glycol | 42 | 21 | 21 | 21 | 21 | 31 | 31 |
| Buffer | | | | | | | |
| Lactic Acid | 1.7 | 1.7 | 1.7 | 1.7 | 1.7 | 1.0 | 0.8 |
| Sodium Hydroxide | q.s. pH 4.0 | q.s. pH 4.0 | q.s. pH 4.0 | q.s. pH 4.0 | q.s. pH 4.0 | q.s. pH 4.0 | q.s. pH 4.0 |
| Preservative | | | | | | | |
| Methyl Paraben | — | — | — | — | — | — | — |
| Diluent | | | | | | | |
| $H_2O$ | qs | qs | qs | qs | qs | qs | qs |

TABLE II

| Ingredient | Acceptable Dezocine Formulations - % (wt/vol) | | | | | |
|---|---|---|---|---|---|---|
| Dezocine | 0.5 | 1.0 | 1.5 | 0.5 | 1.0 | 1.0 |
| Antioxidant | | | | | | |
| Sodium Metabisulfite | 0.015 | 0.015 | 0.0075 | — | — | — |
| Solubilizing Agents | | | | | | |
| Propylene Glycol | 31 | 31 | 31 | 31 | 31 | 31 |
| Buffer | | | | | | |
| Lactic Acid | 0.6 | 0.8 | 1.0 | 0.6 | 0.8 | 1.0 |
| Sodium Hydroxide | q.s. pH 4.0 | q.s. pH 4.0 | q.s. pH 4.0 | q.s. pH 4.0 | q.s. pH 4.0 | q.s. pH 4.0 |
| Diluent | | | | | | |
| $H_2O$ | qs | qs | qs | qs | qs | qs |

What is claimed is:

1. A parenterally acceptable, aqueous composition consisting essentially of from 0.2 to about 2.0 percent weight/volume of (—)-13$\beta$-amino-5,6,7,8,9,10,11,12- octahydro-5α-methyl-5,11-methanobenzocyclodecen-3-ol; from about 30 to about 45 percent weight/volume propylene glycol; from about 0.5 to about 2.0 percent weight/volume of lactic acid buffered with a pharmaceutically acceptable base to afford a pH of from about 3.5 to about 5.0; and from 0 to 0.02 percent weight/volume of sodium or potassium metabisulfite, in water for injection.

2. A composition of claim 1 which contains about 0.0075 to about 0.015 weight/volume sodium metabisulfite.

3. A composition of claim 1 in which said pharmaceutically acceptable base is sodium hydroxide.

4. A composition of claim 1 consisting essentially of about 0.5 percent weight/volume (−)-13β-amino-5,6,7,8,9,10,11,12-octahydro-5α-methyl-5,11-methanobenzocyclodecen-3-ol; about 0.015 percent weight/volume sodium metabisulfite; about 31 percent weight/volume propylene glycol; about 0.6 percent weight/volume lactic acid; sufficient sodium hydroxide to afford a pH of about 4.0 and sufficient water for injection to afford an aqueous solution containing the recited ingredient concentration.

5. A composition of claim 1 consisting essentially of about 1.0 percent weight/volume (−)-13β-amino-5,6,7,8,9,10,11,12-octahydro-5α-methyl-5,11-methanobenzocyclodecen-3-ol; about 0.015 percent weight/volume sodium metabisulfite; about 31 percent weight/volume propylene glycol; about 0.8 percent weight/volume lactic acid; sufficient sodium hydroxide to afford a pH of about 4.0 and sufficient water for injection to afford an aqueous solution containing the recited ingredient concentration.

6. A composition of claim 1 consisting essentially of about 1.5 percent weight/volume (−)-13β-amino-5,6,7,8,9,10,11,12-octahydro-5α-methyl-5,11-methanobenzocyclodecen-3-ol; about 0.0075 percent weight/volume sodium metabisulfite; about 31 percent weight/volume propylene glycol; about 1.0 percent weight/volume lactic acid; sufficient sodium hydroxide to afford a pH of about 4.0 and sufficient water for injection to afford an aqueous solution containing the recited ingredient concentration.

* * * * *